US009932319B2

(12) United States Patent
Adam et al.

(10) Patent No.: US 9,932,319 B2
(45) Date of Patent: Apr. 3, 2018

(54) ANTIOXIDANT HUMIC ACID DERIVATIVES AND METHODS OF PREPARATION AND USE

(71) Applicant: EMPIRE TECHNOLOGY DEVELOPMENT LLC, Wilmington, DE (US)

(72) Inventors: Georgius Abidal Adam, Edensor Park (AU); Scott Andrew Needham, Mangerton (AU)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/894,616

(22) PCT Filed: May 28, 2013

(86) PCT No.: PCT/US2013/042807
§ 371 (c)(1),
(2) Date: Nov. 30, 2015

(87) PCT Pub. No.: WO2014/193337
PCT Pub. Date: Dec. 4, 2014

(65) Prior Publication Data
US 2016/0102069 A1 Apr. 14, 2016

(51) Int. Cl.
C07D 307/77 (2006.01)
C07D 265/38 (2006.01)
C07D 413/14 (2006.01)
C07D 209/36 (2006.01)
C07D 307/91 (2006.01)
A61Q 19/08 (2006.01)
C07C 65/105 (2006.01)
C08K 5/1535 (2006.01)
C08K 5/3417 (2006.01)
C08K 5/357 (2006.01)
A23L 3/3463 (2006.01)
A23L 3/3526 (2006.01)
A23L 3/3544 (2006.01)
A61K 8/368 (2006.01)
A61K 8/49 (2006.01)
A61Q 1/04 (2006.01)
A61Q 1/06 (2006.01)
A61Q 1/08 (2006.01)
A61Q 1/10 (2006.01)
A61Q 1/14 (2006.01)
A61Q 3/02 (2006.01)
A61Q 5/00 (2006.01)
A61Q 5/02 (2006.01)
A61Q 5/06 (2006.01)
A61Q 5/12 (2006.01)
A61Q 19/00 (2006.01)
A61Q 19/04 (2006.01)
A61Q 19/10 (2006.01)

(52) U.S. Cl.
CPC .......... C07D 307/77 (2013.01); A23L 3/3463 (2013.01); A23L 3/3526 (2013.01); A23L 3/3544 (2013.01); A61K 8/368 (2013.01); A61K 8/49 (2013.01); A61K 8/492 (2013.01); A61K 8/4973 (2013.01); A61Q 1/04 (2013.01); A61Q 1/06 (2013.01); A61Q 1/08 (2013.01); A61Q 1/10 (2013.01); A61Q 1/14 (2013.01); A61Q 3/02 (2013.01); A61Q 5/006 (2013.01); A61Q 5/02 (2013.01); A61Q 5/06 (2013.01); A61Q 5/065 (2013.01); A61Q 5/12 (2013.01); A61Q 19/00 (2013.01); A61Q 19/001 (2013.01); A61Q 19/04 (2013.01); A61Q 19/08 (2013.01); A61Q 19/10 (2013.01); C07C 65/105 (2013.01); C07D 209/36 (2013.01); C07D 265/38 (2013.01); C07D 307/91 (2013.01); C07D 413/14 (2013.01); C08K 5/1535 (2013.01); C08K 5/3417 (2013.01); C08K 5/357 (2013.01); A61K 2800/28 (2013.01); A61K 2800/522 (2013.01)

(58) Field of Classification Search
CPC .. C07D 265/38; C07D 413/14; C07D 307/07; C07D 307/77; C07D 307/91
USPC .......................... 544/102; 548/469; 549/456
See application file for complete search history.

(56) References Cited

U.S. PATENT DOCUMENTS 2,586,274 A 2/1952 Tollenaar
4,280,008 A 7/1981 Schoellkopf et al.
4,401,754 A 8/1983 Suzuki et al.
(Continued)

FOREIGN PATENT DOCUMENTS

CN 102432306 A 5/2012
CN 102863687 A 1/2013
(Continued)

OTHER PUBLICATIONS

Verhagen et al., Butylated hydroxyanisole in perspective, Chemico-Biological Interactions (1991), 80(2) pp. 109-134.
(Continued)

Primary Examiner — Venkataraman Balasubramanian
(74) Attorney, Agent, or Firm — Pepper Hamilton LLP

(57) ABSTRACT

Disclosed are antioxidative, natural compounds, their salts, chelates and cleavage derivatives that exhibit a superior combination of properties. The compounds can be used for a variety of purposes, including stabilizing foods, cosmetics, beverages and nutritional supplement. The compounds can be prepared by substantially cleaving a humic acid of formula I to provide at least one antioxidant compounds of formula II, formula III, formula IV, formula V, formula VI, salts, or chelates thereof.

23 Claims, No Drawings

(56) References Cited

U.S. PATENT DOCUMENTS

| | | | |
|---|---|---|---|
| 4,489,155 | A | 12/1984 | Sakanoue et al. |
| 4,671,883 | A | 6/1987 | Connell et al. |
| 4,739,097 | A | 4/1988 | Sander et al. |
| 5,034,045 | A | 7/1991 | Alexander |
| 5,362,615 | A | 11/1994 | Hagemann et al. |
| 5,463,129 | A | 10/1995 | Lysenko et al. |
| 6,297,396 | B1 | 10/2001 | Sas et al. |
| 6,569,900 | B1 | 5/2003 | Dekker et al. |
| 7,192,455 | B2 | 3/2007 | Plos et al. |
| 8,211,558 | B2 | 7/2012 | Yoshimura |
| 2004/0115334 | A1 | 6/2004 | Olmedo |
| 2004/0224844 | A1 | 11/2004 | Bickers et al. |
| 2005/0069974 | A1 | 3/2005 | Gladkov et al. |
| 2006/0058566 | A1 | 3/2006 | Shulgin et al. |
| 2006/0286046 | A1 | 12/2006 | Haber |
| 2007/0212434 | A1 | 9/2007 | Day et al. |
| 2009/0110802 | A1 | 4/2009 | Pibarot et al. |
| 2009/0306361 | A1 | 12/2009 | Kawabe et al. |
| 2010/0035887 | A1 | 2/2010 | Ricciardi |
| 2010/0119653 | A1 | 5/2010 | Hall |
| 2011/0031188 | A1 | 2/2011 | Perminova et al. |
| 2011/0111066 | A1 | 5/2011 | Ferguson et al. |
| 2012/0149697 | A1 | 6/2012 | Legname et al. |
| 2012/0220752 | A1 | 8/2012 | Schutt |
| 2016/0108010 | A1* | 4/2016 | Adam .................. C07D 413/14 544/102 |

FOREIGN PATENT DOCUMENTS

| | | |
|---|---|---|
| DE | 2658941 A1 | 7/1978 |
| EP | 203607 A1 | 12/1986 |
| JP | 6145697 A | 5/1954 |
| JP | S58173138 A | 10/1983 |
| JP | H06211746 A | 8/1994 |
| JP | H06222553 A | 8/1994 |
| JP | H07330669 A | 12/1995 |
| JP | H08188553 A | 7/1996 |
| JP | H09227450 A | 9/1997 |
| JP | 2000086579 A | 3/2000 |
| JP | 2003049196 A | 2/2003 |
| JP | 2004352973 A | 12/2004 |
| JP | 2005272471 A | 10/2005 |
| JP | 2006328298 A | 12/2006 |
| JP | 2009298727 A | 12/2009 |
| WO | 9531192 A1 | 11/1995 |
| WO | 9925191 A1 | 5/1999 |
| WO | 9965702 A1 | 12/1999 |
| WO | 2001034094 A2 | 5/2001 |
| WO | 2005118511 A2 | 12/2005 |
| WO | 2011028495 A1 | 3/2011 |
| WO | 2014193337 A1 | 12/2014 |

OTHER PUBLICATIONS

Vitamin C in Food Processing, accessed at http://web.archive.org/web/20120916175528/http://www.mratcliffe.com/images/vcb.pdf accessed on Mar. 15, 2016, pp. 5.

What is Fulvic Acid?, Supremefulvic.com accessed at https://web.archive.org/web/20150319160405/http://www.supremefulvic.com/documents/pdf/1.what.is.fulvic.acid.pdf accessed on Mar. 15, 2016, pp. 17.

Willard and Fryhle et al., Boron trihalide-methyl sulfide complexes as convenient reagents for dealkylation of aryl ethers, Tetrahedron Letters (1980), 21(39) pp. 3731-3734.

International Search Report and Written Opinion for International application No. PCT/US2013/042807, mailed on Jan. 24, 2014.

Kacker et al., Structural characterisation of humic acid-bound PAH residues in soil by 132C-CPMAS-NMR Spectroscopy; evidence of covalent bonds, Chemosphere (2002), 48(1):117-131.

Adam et al., Humic substances as new stabilisers for polyvinylchloride, Thermochima Acta (Mar. 1, 1986), 99 pp. 217-222.

Aeschbarer et al., Antioxidant properties of humic substance, Environmental Science and Technology (Jan. 1, 2012), 46(9) pp. 4916-4925.

Aguilar et al., Chromium(III)-, iron(II)- and selenium-humic acid/fulvic acid chelate and supplemented humifulvate added for nutritional purposes to food supplements, The EFSA Journal (Jun. 5, 2009), 1147 pp. 1-36.

Avvakumova et al., Antioxidant Properties of Humic Substances Isolated Form Peloids, Pharmaceutical Chemistry Journal (Mar. 2011), 45(3) pp. 192-193.

Babler et al., Reductive cleavage versus hydrogenation of allyl aryl ethers and allylic esters using sodium borohydride/catalytic ruthenium(III) in various aqueous solvent mixtures, Tetrahedron Letters (Feb. 16, 2011), 52(7) pp. 745-748.

Badary et al., Thymoquinone is a potent superoxide anion scavenger, Drug & Chemical Toxicology (May 2003), 26(2) pp. 87-98.

Bernard et al., Dealkylation of Activated Alkyl Aryl Ethers Using Lithium Chloride in Dimethylformamide, Synthesis (Apr. 1989), 1989(4) pp. 287-289.

BHT Product Description, Wholesale Nutrition, accessed at https://web.archive.org/web/20130509093835/http://www.nutri.com/index.cfm/product/31_17/bht.cfm accessed on Mar. 15, 2016, pp. 2.

BioAg Fulvic & Humic Solutions, accessed at https://web.archive.org/web/20120621081858/http://www.bioag.com/teamfulvic/fulvicresearch.html accessed on Mar. 15, 2016, pp. 3.

Bisig, Plasticizer Market Update, BASF Corporation (Jul. 19-21, 2009), pp. 20.

D'Arcgivio et al., Polyphenols, dietary sources and Bioavailability, Ann 1st Super Sanita (2007), 43(4) pp. 348-361.

Densley, Plasticisers in our food &&, Green Left, accessed at https://web.archive.org/web/20101108234729/http://www.greenleft.org.au/node/11274, Aug. 14, 1996, pp. 2.

Duffus, Heavy-metals—A meaningless term, Chemistry and Human Health Division Clinical Chemistry Section, Commission on Toxicology (2002), 74(5) pp. 793-807.

Extended European Search Report for European Application No. 13885836.0 mailed on Feb. 17, 2016.

Fang et al., Lithium chloride-catalyzed selective demethylation of aryl methyl ethers under microwave irradiation, Journal of Molecular Catalysis A: Chemical (Sep. 3, 2007), 274(1-2) p. 16-23.

Folic acid fact sheet, epublications accessed at https://web.archive.org/web/20130429034307/http://www.womenshealth.gov/publications/our-publications/fact-sheet/folic-acid.html content last updated Jul. 16, 2012, pp. 6.

Fulvic Acid A Substance Critical to Human Health, accessed at http://web.archive.org/web/20110910224221/http://www.realrawfood.com/sites/default/files/article/Fulvic%20Acid%20Report.pdf accessed on Dec. 11, 2015, pp. 48.

Fulvic Acid Benefits, accessed at https://web.archive.org/web/20130525140616/http://www.supremefulvic.com/documents/html/fulvic_acid.php, accessed on Mar. 15, 2016, pp. 22.

Fulvic acid the miracle molecule, Supremefulvic.com accessed at https://web.archive.org/web/20120329231513/http://www.supremefulvic.com/documents/pdf/8.fulvic.acid.report.pdf accessed on Mar. 15, 2016, pp. 44.

Fulvic acid, Encyclopedia Britannica accessed at http://www.britannica.com/science/fulvic-acid accessed on Mar. 15, 2016, pp. 2.

Global Trends in Polymer Additives, accessed at http://www.plastemart.com/Plastic-Technical-Article.asp?LiteratureID=1514&Paper=global-trends-in-polymer-additives, Oct. 29, 2010, pp. 2.

How You Rot & Rust, accessed at https://web.archive.org/web/20130302050256/http://biomedx.com/microscopes/rrintro/rr1.html, accessed on Mar. 15, 2016, pp. 1.

Humic & Fulvic Acids:The Black Gold of Agriculture, accessed at http://web.archive.org/web/20120417060303/http://www.humintech.com/pdf/humicfulvicacids.pdf accessed on Mar. 15, 2016, pp. 10.

Humic & Fulvic Substances I, Supremefulvic.com accessed at http://www.supremefulvic.com/documents/pdf/2.about.humic-fulvic.substances.1.pdf, accessed on Mar. 15, 2016, pp. 35.

Humic & Fulvic Substances II, Supremefulvic.com accessed at http://www.supremefulvic.com/documents/pdf/2.about.humic-fulvic.substances.1.pdf, accessed on Mar. 15, 2016, pp. 38.

(56) References Cited

OTHER PUBLICATIONS

International Search Report and Written Opinion for International Application No. PCT/US2013/042814 mailed Jan. 31, 2014.
International Search Report and Written Opinion for International Application No. PCT/US2013/042807 mailed Jan. 24, 2014.
Investigation of humic acid N with X-ray photoelectron spectroscopy: Effect of acid hydrolysis an comparison with 15N cross polarization/ magic angle spinning nuclear magnetic resonance spectroscopy, International Atomic energy Agency, Technical Report Series, International Atomic Energy Agency, Vienna (Jul. 2006), 47(4) p. 263.
It's Perfectly Clear the Case Against PVC Packaging, Masspirg, accessed at https://web.archive.org/web/20050305121509/http://www.pirg.org/masspirg/enviro/sw/pvc/, accessed on Mar. 15, 2016, pp. 2.
Kacker et al., Structural characterisation of humic acid-bound PAH residues in soil by 13C-CPMAS-NMR-spectroscopy: evidence of covalent bonds, Chemosphere (2002), 48(1) pp. 117-131.
Klocking and Helbig, Medical aspects and applications of Humic substances, accessed at http://www.supremefulvic.com/documents/pdf/5.medical.aspects.and.applications.of.humic.substances.pdf, accessed on Mar. 15, 2016, pp. 2.
List of food additives, accessed at http://web.archive.org/web/20130424122000/http://en.wikipedia.org/wiki/List_of_food_additives last modified on Mar. 3, 2013, pp. 15.
Manach et al., Polyphenols: food sources and bioavailability1,2, American Journal of Clinical Nutrition (May 2004), 79(5) pp. 727-747.
Marton and Alder, Carbonyl Groups in Lignin. III. Mild Catalytic Hydrogenation of Björkman Lignin, Acta Chemica Scandinavica (1961), 15(2) pp. 370-383.
Okubo et al., Cell death induced by the phenolic antioxidant tert-butylhydroquinone and its metabolite tert-butylquinone in human monocytic leukemia u937 cells, Food and Chemical toxicology (May 2003), 41(5) pp. 679-688.
Pena-Mendez et al., Humic substances-compounds of still unknown structure: applications in agriculture, industry, environment, and biomedicine, Journal of Applied Biomedicine. (Nov. 22, 2004), 3(1) pp. 13-24.
Pettit, Organic Matter, Humus, Humate, Humic Acid, Fulvic Acid and Humin: Their Importance in Soil Fertility and Plant Health, accessed at http://www.humates.com/pdf/ORGANICMATTERPettit.pdf, accessed on Mar. 15, 2016, pp. 17.
pH and Acidosis, Supremefulvic.com accessed at https://web.archive.org/web/20090922095505/http://www.supremefulvic.com/documents/html/pHbyDrLam.html, accessed on Mar. 15, 2016, pp. 5.
pH and Cancer, accessed at http://www.supremefulvic.com/documents/pdf/11.ph.and.cancer.pdf, accessed on Mar. 15, 2016, pp. 3.
Rath et al., Effects of humic acid on broiler chickens, Poultry Science (Mar. 2006), 85(3) pp. 410-414.
Reische et al., Antioxidants, in Food Lipids Chemistry, Nutrition, and Biotechnology, Third edition, CRC press (1998), pp. 409-433.
Root of All Disease, Supremefulvic.com accessed at http://www.supremefulvic.com/documents/pdf/7.the.root.of.all.disease(edited).pdf, accessed on Mar. 15, 2016, pp. 19.
Safer and Al-Nughamish, Heptatoxicity induced by the anti-oxidant food additive, butylated hydroxytoluene (BHT), in rates: An electron microscopical study, Histology and Histopatholgly (Apr. 1999), 14(2) pp. 391-406.
Sarafian et al., Synergistic cytotoxicity of Δ9 tetrahydrocannabinol and butylated hydroxyanisole, Toxicology Letters (Jul. 21, 2002), 133 pp. 171-179.
Schneider et al., Inhibition of HIV-1 in Cell Culture by Synthetic Humate Analogues Derived from Hydroquinone : Mechanism of Inhibition, US National Library of Medicine National Institutes of HealthSearch database (Apr. 15, 1996), 218(2) pp. 389-395.
Shahidi and Zhong, Antioxidants: Regulatory Status, in Bailey'S Industrial Oil and Fat Products, 1(6th Edition, Chapter 12) pp. 491-512.
Shahidi et al., Antioxidants, Food Additives Databook (2003), Part 2 pp. 76-83.
Sonnenberg et al., Chemical Degradation of Humic Substances for Structural Characterization, in Aquatic Humic Substances, Chapter 1, Advances in Chemistry (Dec. 15, 1988), 219 pp. 3-23.
Supplementary European Search Report for European Application No. 13885964.0 mailed on Feb. 10, 2016.
The pH Reguatory System of the Body, accessed at http://www.supremefulvic.com/documents/pdf/10.how.you.rot.and.rust.pdf, accessed on Mar. 15, 2016, pp. 28.
Aeschbacher et al., Antioxidant Properties of Humic Substances, Environmental Science and Technology (Mar. 30, 2012), vol. 46 pp. 4916-4925.
Avvakumova et al., Antioxidant Properties of Humic Substances Isolated From Peloids, Pharmaceutical Chemistry Journal (Jun. 2011), 45(3) pp. 192-193.
D'Archivio et al., Polyphenols, Dietary Sources and Bioavailability, Ann. Ist. Super. Sanita. (2007), 43(4) pp. 348-361.
Supplementary Partial European Search Report issued for EP13885964.0 dated Feb. 10, 2016.
"Fulvic acid Chemical compound," Encyclopedia Britannica, accessed at http://www.britannica.com/science/fulvic-acid, last updated on Dec. 7, 2000, pp. 2.
"Presenting BioVinyl", BioVinyl, accessed at https://web.archive.org/web/20130529024757/http://www.biovinyl.com/, achrived on May 29, 2013, accessed on Mar. 4, 2016, p. 2.
"Tannins derivates," Ajinomoto, accessed at https://web.archive.Org/web/20120318055927/http://www.natural-specialities.com/natural-specialities/en/8457-tannins-derivates.html, achirved on Mar. 18, 2012, accessed on Mar. 4, 2016, p. 1.
"6 Food Ingredient Mega Trends," Natural Products Insider, accessed at http://www.naturalproductsinsider.com/news/2010/09/6-food-ingredient-mega-trends.aspx, posted on Sep. 30, 2010, pp. 2.
Alvarez-Puebla. R.A., et al., "Theoretical study on fulvic acid structure, conformation and aggregation: A molecular modelling approach," Science of the Total Environment ,vol. 358, Issue. 1-3, pp. 243-254 (Apr. 1, 2006).
Atalay, Y.B., et al., "Distribution of Proton Dissociation Constants for Model Humic and Fulvic Acid Molecules," Environmental Science & Technology, vol. 43, Issue 10, pp. 3626-3631 (Apr. 17, 2009).
Faust, R.H., "Fulvic acid solution WuJinSan crucial cellular antioxidant," pp. 4 (2006).
Giovanela, M., et al., " Elemental compositions FT-IR spectra and thermal behavior of sedimentary fulvic and humic acids from aquatic and terrestrial environments," Geochemical Journal , vol. 38, Issue 3, pp. 255-264 (2004).
Gregor, J. E., and Powell. H.K.J., "Effects of Extraction Procedures on Fulvic Acid Properties," Science of the total Environment , vol. 62, pp. 3-12 (1987).
Hua, Li, "Development and Application of Peat Humic Acid in Plastics Industry," HeBei Chemical Engineering, vol. 2, pp. 47-48 (1990).
International Search Report and Written Opinion for International Application No. PCT/US2013/048604 dated Feb. 25, 2014, pp. 7.
International Search Report and Written Opinion for International Application No. PCT/US2013/037144 dated Nov. 5, 2013, pp. 13.
Kiprop, A., et al., "Synthesis of Humic and Fulvic Acids and their Characterization using Optical Spectroscopy (ATR-FTIF and UV-Visible)," International Journal of Applied Science and Technology, vol. 3, Issue. 8, pp. 28-35 (Dec. 1, 2013).
Kohut-Svelko, N., et al., "Overview of the preparation of pure polyaniline and conductive composites in dispersed media and by thermal processes: from laboratory to semi-industrial scale," Polymer international, vol. 55, Issue 10, pp. 1184-1190 (Oct. 2006).
Kucerik, J., et al., "Antioxidant effect of lignite humic acids and its salts on the thermo-oxidative stability/degradation of polyvinyl alcohol blends," Environmental Chemistry Letters , vol. 6, Issue 4, pp. 241-245 (Nov. 2008).
Leenheer, J.A., et al., "Molecular Resolution and Fragmentation of Fulvic Acid by Electrospray Ionization/Multistage Tandem Mass Spectrometry," Analytical Chemistry ,vol. 73, Issue 7, pp. 1461-1471 (Mar. 7, 2001).

(56) References Cited

OTHER PUBLICATIONS

Lundin, L. et al., "Understanding food structure and function in developing food for appetite control," Nutrition and Dietetics, vol. 65, Issue s3, pp. S79-S85 (Jun. 2008).

Peng et al., "Production of Plastics by Regeneration of Humic Acid through Coal Nitration," Chinese Coal, vol. 25, Issue 4, pp. 39-40 (1999).

Rodriguez, N.C., et al., "Antioxidant activity of fulvic acid: a living matter-derived bioactive compound," Journal of Food, Agriculture & Environment, vol. 9, Issue 3-4, pp. 123-127 (Jul. 1, 2011).

Salmonella, C.E., "Food poisoning", accessed at http://web.archive.org/web/20120925125222/http://www.markusrothkranz.com/freebies/foodpoisoning.pdf, archived on Sep. 25, 2012, accessed on May 11, 2017, pp. 7.

Schepetkin, I.A., et al., "Characterization and Biological Activities of Humic Substances from Mumie," Journal of Agricultural and Food Chemistry., vol. 51, No. 18, pp. 5245-5254 (Aug. 27, 2003).

Speijers, G.J.A., and Apledoorn, M.E.V., "Gallates (Propyl, Octyl and Dodecyl)," Inchem, accessed at https://web.archive.org/web/20130619094846/http://www.inchem.org/documents/jecfa/jecmono/v32je02.htm, archived on Jun. 19, 2013, accessed on Mar. 4, 2016, pp. 16.

Supplementary European Search Report for European Application No. 13882133.5 dated Nov. 10, 2016, pp. 9.

Supplementary European Search Report for European Application No. 13888488.7 dated Jan. 30, 2017, pp. 8.

Zhipei, "Plastic Additive," Jian Xi Humic Acid, pp. 66 (1985).

\* cited by examiner

ANTIOXIDANT HUMIC ACID DERIVATIVES AND METHODS OF PREPARATION AND USE

CLAIM OF PRIORITY

This application is a U.S. national stage filing under 35 U.S.C. § 371 of International Application No. PCT/US2013/042807 filed on May 28, 2013 entitled "ANTIOXIDANT HUMIC ACID DERIVATIVES AND METHODS OF PREPARATION AND USE," which is incorporated herein by reference in its entirety.

BACKGROUND

Various types of antioxidant additives are used to protect food from oxidation, inhibiting the effect of oxygen in the atmosphere. Natural preservatives, such as soluble vitamin C (ascorbic acid and its salts with sodium, calcium, etc.), may be used to protect some fruits or meat, or while ascorbic stearate or palmitate are used as oil or fat soluble antioxidants for use with other foods. Ascorbic acid (Vitamin C) and tocopherols (a class of compounds with Vitamin E activity) are the most important commercial natural antioxidants, but they are expensive and unstable in processing and storage at high temperatures.

The expense of current natural preservatives limits their broader use in foods, leading to continued use of synthetic preservatives. Synthetic anti-oxidants include BHT (butylated hydroxytoluene), TBHQ (t-butyl hydroquinone), BHA (butylated hydroxy anisole), gallic acid, and gallic esters. The benefits and safety of many artificial food additives (including preservatives) are the subject of debate among academics and regulators specializing in food science and toxicology.

SUMMARY

New antioxidants for use in food processing ideally are nontoxic, inexpensive, effective at low concentration (0.001-0.02%), survive processing, stable in finished products, be devoid of undesirable color, flavor, and odor effects, and most importantly be compatible with food products. This disclosure details a natural source of inexpensive food preservatives based on humic acid derivatives, and their salts and chelates. These compounds are stable, non-toxic, have high bioavailability, and are suitable for both oil and water based foods due to good solubility at all pH in both water and oil.

It has been found that subjecting humic acid to selective aryl ether cleavage conditions creates compounds that meet all the above described criteria for anti-oxidative food preservatives. The anti-oxidation efficiency of these derivatives is due to their chemical structure which contains functional groups known as antioxidant and free radical scavenger active groups. The humate derivatives demonstrate higher efficiency as an anti-oxidant than humic acid itself, have highly stable activities, are highly nutritious, and have tremendous potential as food additives as well as anti-oxidant/thermal stabilizers for various polymer systems, particularly food-safe polymeric packaging.

Embodiments thus provide methods for stabilizing foods, beverages, cosmetics and/or nutritional supplements by the application of humic acid cleavage derived compounds or compositions, in an amount sufficient to have a measurable stabilizing effect.

Other embodiments further provide stabilized foods, beverages, cosmetics and/or nutritional supplements comprising a food, beverage, cosmetic and/or nutritional supplement, together with a stabilizing composition consisting of antioxidants derived from cleavage of humic acid.

Embodiments include methods for stabilizing the fresh flavor and preventing the formation of off-flavors in a food product matrix, such as in a dairy product, fat, oil, fat emulsion, edible ice, fruit, vegetable, fungi, seaweed, nuts, seeds, confectionery, cereal, cereal product derived from cereal grains, bakery ware, meat, meat byproduct, fish, fish product, egg product, sugar, artificial sweetener, spices, condiment, soup, sauce, salad, protein mix, non-dairy beverage, or savory snack. The food products are treated at some stage in their production with an effective amount of an antioxidant composition derived from cleavage of select aryl-heteroatom humic acid; in a manner which does not adversely impact the taste or color of the foods.

Other embodiments provide methods for stabilizing the fresh flavor and color and preventing the formation of off-flavors and off-colors in a food product matrix such as a vegetable oil, animal fat, processed cheeses, chewing gum base, processed meat products, dried meats, sausages, beef patties, meatballs, frozen seafood, pizza toppings, protein, yeast, bakery products, dry cereals, spices, dehydrated potatoes, potato chips, beverage mixes, nonalcoholic beverages, mixed nuts, fruit, vegetables, butter, margarine, dairy products, and the like, by incorporating into these materials at some stage in their production, an effective amount of one or more antioxidant compounds derived from cleavage of humic acid.

DETAILED DESCRIPTION

The above summary of the present technology is not intended to describe each illustrated embodiment or every possible implementation of the present technology. The detailed description, which follows, particularly exemplifies these embodiments.

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

The term "alkyl" or "alkyl group" refers to a branched or unbranched hydrocarbon or group of 1 to 20 carbon atoms, such as but not limited to methyl, ethyl, n-propyl, isopropyl, n-butyl, isobutyl, t-butyl, octyl, decyl, tetradecyl, hexadecyl, eicosyl, tetracosyl and the like. "Cycloalkyl" or "cycloalkyl groups" are branched or unbranched hydrocarbons in which all or some of the carbons are arranged in a ring, such as but not limited to cyclopentyl, cyclohexyl, methylcyclohexyl and the like. The term "lower alkyl" includes an alkyl group of 1 to 6 carbon atoms.

"Substituent" refers to a molecular nontoxic group that replaces a hydrogen in a compound and may include, but is not limited to, $C_1$-$C_{20}$ alkyl. The term "substituted alkyl" is used herein to allow for the presence of one or more additional substituents on an alkyl group.

"Optional" or "optionally" means that the subsequently described event or circumstance may or may not occur, and that the description includes instances where the event occurs and instances where it does not.

The term "halide" as used herein refers to the halogens fluorine, chlorine, bromine, and iodine.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

As used herein the term 'transition metal" should be understood to include elements that are nontoxic non heavy metals or radioactive of the Periodic Table. In chemical terms, these are elements having a partially filled inner shell of electrons. The term "transition metal chelate" as used herein generally means a transition metal cation and anions that surround the metal cation and are joined to it by electrostatic bonds.

As used herein, the term "stereoisomer" refers to a compound made up of the same atoms bonded by the same bonds but having different three-dimensional structures which are not interchangeable.

Antioxidative compounds, their salts, and chelates useful for stabilizing foods, cosmetics, beverages and nutritional supplements can be prepared from humic acid by cleavage under controlled conditions. The anti-oxidation efficiency of these sustainable natural derivatives is due to their chemical structure which contains functional groups that are known as antioxidant and free radical scavenger active groups. The chemical structure of a humic acid (I) has cleavable groups at C1-C5.

a salt, or chelate thereof, wherein each $R_1$ is independently alkyl.

Cleavage of aryl heteroatom bonds C1-05 of humic acid I leads to compounds II-VI. The compounds are active multi pH buffers since they dissolve at all pH values. The cleavage derivatives of humic acid at one or more of C1-C5, and their carboxylate salts and chelates have lower molecular weight than humic acid. These derivatives also have high oxygen content due to carboxylate groups adjacent to carbonyl or hydroxyl groups. The chemical compounds II-VI demonstrate highly stable activities and are highly nutritious. The low molecular weight structures derived demonstrate a higher efficiency as anti-oxidants than humic acid I, and the chemical compounds II-VI have tremendous potential as food additives as well as anti-oxidant/thermal stabilizers for various polymer systems, particularly food-safe polymeric packaging.

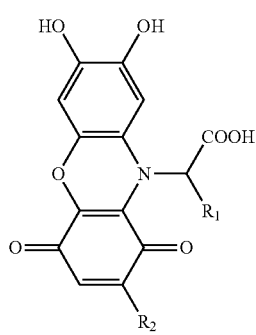

II

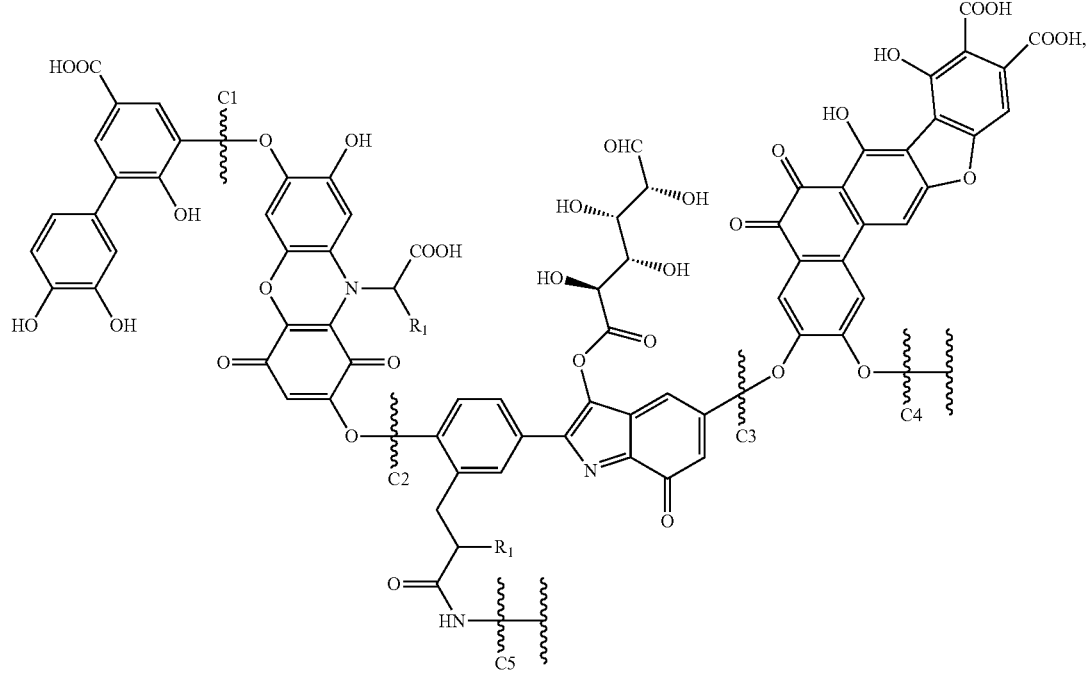

I

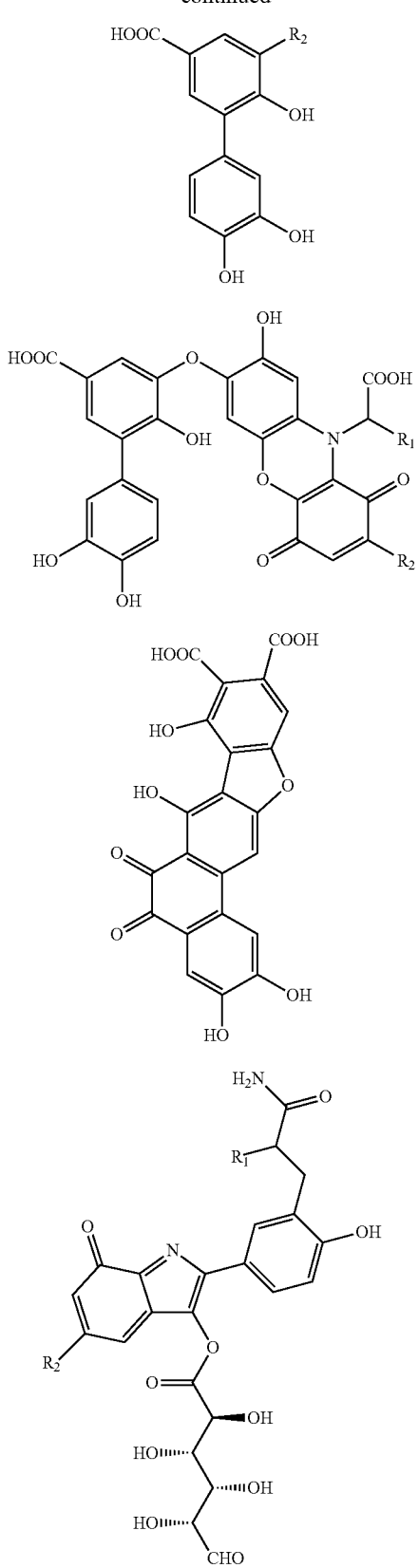

wherein R₁ is alkyl; and R₂ is hydrogen, iodide, or hydroxyl.

The anti-oxidation efficiency of these sustainable natural derivatives is due to their chemical structure which contains all functional groups that are known as antioxidants and free radical scavenger active groups. Humic acid as a basic ingredient for the proposed technology is currently extracted on industrial scale mainly for use as organic fertilizers and plant nutrients. It is sourced cheaply from non-contaminated marsh and forest soils that can contain up to 30-40% humic materials. Furthermore, these compounds have tremendous potential as thermal stabilizers for various polymer systems used in food packaging.

The cleavage derivatives of humic acid I have various uses including as antioxidants for several polymeric systems such as polyvinyl chloride (PVC), polyethylene (PE) and polypropylene (PP). These antioxidants can be used as a solid, solution, chelated with transition (nutrient) metals. The carboxylic acid group can be transformed into carboxylate salts of Na, K, Ca, Zn, Mg, and can form chelates with divalent and trivalent metal ions.

The antioxidants of embodiments from cleavage of humic acid require no necessary purification steps, such as ultrafiltration or desalination, nor fractionation into fractions with distinct molecular weights and high purity. The crude antioxidant cleavage solution unexpectedly, and advantageously, exhibits high activity without any further costly processing. However, purified compounds, their salts, chelates, and cleavage derivatives can potentially exhibit superior characteristics in certain applications.

The humic acid cleavage products provide a stabilizing effect at various doses in foods as they are nontoxic and are nutrients. The antioxidant property in food of the crude extract, allows its usage at various doses, hence, bypassing any undesired color or flavor effect that might arise from the use of the humic acid cleavage compounds as food preservatives.

Humic acid cleavage derivatives can be obtained by a reductive cleavage technique. Chemical compounds II-VI, have active functional groups (quinones, hydroquinones and alkyl phenols) that can act as anti-oxidants and free radical scavengers, chelating groups (via carboxyl groups or hydroxyl groups). It is also noted that the chemical structures detailed below are highly synchronized with that of ascorbic acid (Vitamin C) (see the sugar side group in structure VI); the world's most popular and commonly used as food antioxidant. The chemical compounds II-VI are less expensive to manufacture than ascorbic acid and have the ability to dissolve and bond minerals and other nutritional elements with enhanced bioavailability.

One embodiment is an antioxidant compound. An embodiment comprises at least one compound of formula II, formula III, formula IV, formula V, formula VI, a salt, chelate, or combination thereof, wherein each R₁ are independently alkyl, and each R₂ is independently hydrogen, iodide, or hydroxyl. A certain embodiment is an antioxidant of formula II, a salt, or chelate thereof, wherein R₁ is alkyl, and R₂ is hydrogen, iodide, or hydroxyl. Another embodiment is an antioxidant of formula III, a salt, or chelate thereof, wherein R₂ is hydrogen, iodide, or hydroxyl. Still another embodiment is a compound of formula IV, a salt, or chelate thereof, wherein R₁ is alkyl, and R₂ is hydrogen, iodide, or hydroxyl. Another certain embodiment is a compound of formula V, a salt, or chelate thereof. Another embodiment is a compound of formula VI, a salt, or chelate thereof, wherein R₁ is alkyl, and R₂ is hydrogen, iodide, or hydroxyl. In various embodiments of any one of the above embodiments, $R_1$ is $(C_1$-$C_{20})$alkyl. In other embodiments, $R_1$ is a $(C_1$-$C_6)$alkyl. In still other embodiments, $R_1$ is a $(C_7$-$C_{20})$alkyl. In various embodiments of any one of the above embodiments, $R_2$ is hydrogen. In other embodiments, $R_2$ is iodide. In still other embodiments, $R_2$ is hydroxyl.

In any one of the aforementioned embodiments of the antioxidant compounds, the antioxidant compound may be a salt. In certain non-limiting embodiments, the salt is a lithium salt, sodium salt, ammonium salt, potassium salt, calcium salt, barium salt, magnesium salt, manganese salt, zinc salt, aluminum salt, iron salt, or a combination thereof. In certain embodiments, the salt is a sodium salt, potassium salt, calcium salt, ammonium salt, or combination thereof. In an embodiment, the antioxidant compound is a sodium salt. In another embodiment, the antioxidant compound is a potassium salt. In yet another embodiment, the antioxidant compound is a calcium salt. In still another certain embodiment, the antioxidant compound is an ammonium ion salt. In yet other embodiments of any one of the aforementioned antioxidant compounds, the antioxidant compound may be a transition metal ion chelate. In certain non-limiting embodiments, the transition metal ion chelate is a manganese salt, zinc salt, aluminum salt, iron salt, or a combination thereof.

Another embodiment is a method of preparing an antioxidant compound, the method comprising substantially cleaving a humic acid to form at least one antioxidant compound of formula II, formula III, formula IV, formula V, formula VI, a salt, or chelate thereof. In a further embodiment, the humic acid comprises at least one compound of formula I.

Humic acid having the substructure I (Figure 1) may be cleaved at positions C1, C2, C3, C4, and C5 thereby making useful derivatives. Several types of hydrogenolysis cleaving agents can be used for aryl ethers cleavage (structures present in humic acid molecules) such as nickel-catalyzed hydrogenolysis, sodium borohydride ($NaBH_4$), amide hydro halide salts, lithium chloride in dimethylformamide, hydrogen iodide, and hydrogen bromide, and others.

Some embodiments include forming at least one compound of formula II, formula III, formula IV, formula V, and formula VI as a salt, chelate or combination thereof, wherein each $R_1$ are independently alkyl, and each $R_2$ is independently hydrogen, iodide, or hydroxyl. A certain embodiment is formation of an antioxidant of formula II, a salt, or chelate thereof, wherein $R_1$ is alkyl, and $R_2$ is hydrogen, iodide, or hydroxyl. Another embodiment is formation of an antioxidant of formula III, a salt, or chelate thereof, wherein $R_2$ is hydrogen, iodide, or hydroxyl. Still another embodiment is formation of a compound of formula IV, a salt, or chelate thereof, wherein $R_1$ is alkyl, and $R_2$ is hydrogen, iodide, or hydroxyl. Another certain embodiment is formation of a compound of formula V, a salt, or chelate thereof. Another embodiment is formation of a compound of formula VI, a salt, or chelate thereof, wherein $R_1$ is alkyl, and $R_2$ is hydrogen, iodide, or hydroxyl. In various embodiments of any one of the above methods, $R_1$ is $(C_1-C_{20})$alkyl. In other embodiments, $R_1$ is a $(C_1-C_6)$alkyl. In still other embodiments, $R_1$ is a $(C_7-C_{20})$alkyl. In various embodiments of any one of the above embodiments, $R_2$ is hydrogen. In other embodiments, $R_2$ is iodide. In still other embodiments, $R_2$ is hydroxyl. In certain embodiments of the above compounds, the salt is a lithium salt, sodium salt, ammonium salt, potassium salt, calcium salt, barium salt, magnesium salt, manganese salt, zinc salt, aluminum salt, iron salt, or a combination thereof. In other embodiments, the salt is a sodium salt, potassium salt, calcium salt, ammonium salt, or a combination thereof. In still other embodiments of any one of the above embodiments, the compound is a transition metal ion chelate.

In each of the aforementioned embodiments of the methods of preparation, the method may further comprise isolating at least one of the antioxidant compounds. In other embodiments the isolating prepares a mixture of more than one of the compounds of formula II, formula III, formula IV, formula V, formula VI, a salt, or chelate thereof. In certain non-limiting embodiments, the salt isolated is a lithium salt, sodium salt, ammonium salt, potassium salt, calcium salt, barium salt, magnesium salt, manganese salt, zinc salt, aluminum salt, iron salt, or a combination thereof.

Another embodiment is a stabilized food product comprising at least one antioxidant compound of formula II-VI, a salt, or chelate thereof, wherein $R_1$ is an alkyl, and $R_2$ is hydrogen, iodide, or hydroxyl, in a food product matrix. In a certain embodiment, the food product matrix is a dairy product, fat, oil, fat emulsion, edible ice, fruit, vegetable, fungi, seaweed, nuts, seeds, confectionery, cereal, cereal product derived from cereal grains, bakery ware, meat, meat byproduct, fish, fish product, egg product, sugar, artificial sweetener, spices, condiment, soup, sauce, salad, protein mix, non-dairy beverage, savory snack, or combinations thereof. In another certain embodiment, the food product matrix is a vegetable oil, animal fat, processed cheeses, chewing gum base, processed meat products, dried meats, sausages, beef patties, meatballs, frozen seafood, pizza toppings, protein, yeast, bakery products, dry cereals, spices, dehydrated potatoes, potato chips, beverage mixes, nonalcoholic beverages, mixed nuts, fruit, vegetables, butter, margarine, dairy products, or combinations thereof. In various embodiments of any one of the above stabilized food products, $R_1$ is $(C_1-C_{20})$alkyl. In other embodiments, $R_1$ is a $(C_1-C_6)$alkyl. In still other embodiments, $R_1$ is a $(C_7-C_{20})$ alkyl. In various embodiments of any one of the above embodiments, $R_2$ is hydrogen. In other embodiments, $R_2$ is iodide. In still other embodiments, $R_2$ is hydroxyl.

Yet another embodiment is a stabilized food product comprising at least one antioxidant compound of formula II-VI, a salt, or chelate thereof, wherein $R_1$ is an alkyl, and $R_2$ is hydrogen, iodide, or hydroxyl, in a food product matrix, wherein the antioxidant compound extends the shelf-life of the food product matrix. In still another embodiment, the stabilized food product is stable to about 350° C. In yet another embodiment, the antioxidant compound is present in the food product matrix at a concentration of about 1 percent, about 3000 ppm, about 1000 ppm, about 300 ppm, about 100 ppm, about 30 ppm, about 10 ppm, about 3 ppm, about 1 ppm, or any range between two of the concentrations. In various specific embodiments, the antioxidant is present in a food product at less than about 3000 ppm, less than about 300 ppm, less than about 100 ppm, or less than about 10 ppm.

Another embodiment is a polymeric matrix comprising at least one antioxidant compound of formula II-VI, a salt, or chelate thereof, wherein $R_1$ is an alkyl, and $R_2$ is hydrogen, iodide, or hydroxyl, in combination with a polymer. In some embodiments, the antioxidant compound is an antioxidant. In certain embodiments, the polymer is a polyvinyl chloride, low density polyethylene, high density polyethylene, polyvinyl alcohol, polypropylene, or combination thereof. In yet other embodiments, the polymeric matrix may be suitable for various packaging to extend a shelf life of a product. In certain embodiments, the polymeric matrix is a food packaging. In various embodiments of any one of the above polymeric matrices, $R_1$ is $(C_1-C_{20})$alkyl. In other embodiments, $R_1$ is a $(C_1-C_6)$alkyl. In still other embodiments, $R_1$ is a $(C_7-C_{20})$alkyl. In various embodiments of any one of the above embodiments, $R_2$ is hydrogen. In other embodiments, $R_2$ is iodide. In still other embodiments, $R_2$ is hydroxyl.

In yet another embodiment, the antioxidant compound is present in the polymeric matrix by weight at a concentration of about 5%, about 2.5%, about 1%, about 0.5%, about 1000 ppm, about 300 ppm, about 200 ppm, about 100 ppm, about 30 ppm, about 10 ppm, about 3 ppm, about 1 ppm, or any range between two of the concentrations. In various specific embodiments, the antioxidant is present in a polymer at less than about 5000 ppm, less than about 300 ppm, less than about 100 ppm, or less than about 10 ppm. In certain embodiments, the antioxidant compound is between about 0.02% and about 2.5% by weight of the polymer. In another certain embodiment, the antioxidant compound is between about 0.1% and about 0.5% by weight.

In each of the aforementioned embodiments of the polymeric matrix, the antioxidant compound may be a salt. In certain embodiments, the salt is a lithium salt, sodium salt, ammonium salt, potassium salt, calcium salt, barium salt, magnesium salt, manganese salt, zinc salt, aluminum salt, iron salt, or a combination thereof. In certain embodiments, the salt is a sodium salt, potassium salt, calcium salt, ammonium salt, or combination thereof. In an embodiment, the antioxidant compound is a sodium salt. In another embodiment, the antioxidant compound is a potassium salt. In yet another embodiment, the antioxidant compound is a calcium salt. In still another certain embodiment, the antioxidant compound is an ammonium ion salt. In yet other embodiments of the aforementioned antioxidant compounds, the antioxidant compound may be a transition metal ion chelate. In certain embodiments, the transition metal ion chelate is a manganese salt, zinc salt, aluminum salt, iron salt, or a combination thereof.

Another embodiment is a nutritional supplement comprising at least one antioxidant compound of formula II-VI, a salt, or chelate thereof, wherein $R_1$ is an alkyl, and $R_2$ is hydrogen, iodide, or hydroxyl, in combination with a nutritionally acceptable carrier. In some embodiments, the nutritionally acceptable carrier further comprises a flavoring agent. In other embodiments, the nutritional supplement further comprises buffering agents. In still other embodiments, the nutritional supplement further comprises minerals. Yet other embodiments are wherein the antioxidant compound is a salt, chelate, or combination thereof. Further, in some embodiments, the salt is a lithium salt, sodium salt, ammonium salt, potassium salt, calcium salt, barium salt, magnesium salt, manganese salt, zinc salt, aluminum salt, iron salt, or a combination thereof. By nutritional supplements we include as examples, but are not limited to: eye health supplements, vitamins, nutrition boosters, carotenoid supplements, protein supplements, energy bars, nutritional bars, algal oils, fish oils, and oils containing polyunsaturated fatty acids. In various embodiments of any one of the above nutritional supplements, $R_1$ is $(C_1-C_{20})$alkyl. In other embodiments, $R_1$ is a $(C_1-C_6)$alkyl. In still other embodiments, $R_1$ is a $(C_7-C_{20})$alkyl. In various embodiments of any one of the above embodiments, $R_2$ is hydrogen. In other embodiments, $R_2$ is iodide. In still other embodiments, $R_2$ is hydroxyl.

Yet another embodiment is a method of preparing a stabilized food product comprising adding at least one antioxidant compound of formula II-VI, a salt, or chelate thereof, wherein $R_1$ is an alkyl, and $R_2$ is hydrogen, iodide, or hydroxyl, to a food product matrix. In certain embodiments, the compound is a salt, chelate, or combination thereof. In some embodiments, the food product matrix is a dairy product, fat, oil, fat emulsion, edible ice, fruit, vegetable, fungi, seaweed, nuts, seeds, confectionery, cereal, cereal product derived from cereal grains, bakery ware, meat, meat byproduct, fish, fish product, egg product, sugar, artificial sweetener, spices, condiment, soup, sauce, salad, protein mix, non-dairy beverage, savory snack, or combinations thereof. In other embodiments, the food product matrix is a vegetable oil, animal fat, processed cheeses, chewing gum base, processed meat products, dried meats, sausages, beef patties, meatballs, frozen seafood, pizza toppings, protein, yeast, bakery products, dry cereals, spices, dehydrated potatoes, potato chips, beverage mixes, nonalcoholic beverages, mixed nuts, fruit, vegetables, butter, margarine, dairy products, or combinations thereof.

The instant humic aid cleavage compounds may be added to foods, including animal foods. By foods, we mean both human and animal foods. Human foods may include as non-limiting examples: meat (wild and domestic; fresh and cured, processed and unprocessed, dried, canned), Poultry, fish, vegetable protein, dairy products (milk, cheese, yogurt, ice cream), ground spices, vegetables, pickles, mayonnaise, sauces (pasta sauces, tomato based sauces), salad dressings, dried fruits, nuts, potato flakes, soups, baked goods (breads, pastries, pie crusts, rolls, cookies, crackers, cakes, pies, bagels), vegetable oils, frying oil, fried foods (potato chips, corn chips), prepared cereals (breakfast cereals), cereal grain meals, condiments (ketchup, mustard, cocktail sauce, candies, confectionary, chocolates, baby foods). Animal foods may include as non-limiting examples: extruded pet food, kibbles, dry pet food, semi-dry pet food, and wet pet food.

The instant humic acid cleavage compounds may be added directly to foods according to the solubility characteristics. They may be dissolved in a carrier, such as an alkylene glycol, glycerin, food grade surfactants, benzyl alcohol, and the like, and then added to foods. They can be dispersed onto solid carriers, such as salt, flour, sugars, maltodextrin, silica (such as CABOSIL™), cyclodextrins, starches, gelatins, lactose, whey powders, proteins, and the like and then added to foods.

In various embodiments of any one of the above methods, $R_1$ is $(C_1-C_{20})$alkyl. In other embodiments, $R_1$ is a $(C_1-C_6)$ alkyl. In still other embodiments, $R_1$ is a $(C_7-C_{20})$alkyl. In various embodiments of any one of the above embodiments, $R_2$ is hydrogen. In other embodiments, $R_2$ is iodide. In still other embodiments, $R_2$ is hydroxyl.

Yet another embodiment is a method for preparing a wherein the antioxidant extends the shelf-life of the food product matrix. In still another embodiment, the method produces a stabilized food product that is stable to about 250-350° C. In yet another embodiment, the method comprises adding the antioxidant compound to the food product matrix at a concentration of about 1 percent, about 3000 ppm, about 1000 ppm, about 300 ppm, about 100 ppm, about 30 ppm, about 10 ppm, about 3 ppm, about 1 ppm, or any range between two of the concentrations. In various embodiments, the antioxidant is present in a food product at less than about 3000 ppm, less than about 300 ppm, less than about 100 ppm, or less than about 10 ppm.

The instant humic acid cleavable compounds may be added to cosmetics. By cosmetics we include as non-limiting examples: lip balm, lip gloss, lipstick, lip stains, lip tint, blush, bronzers & highlighters, concealers & neutralizers, foundations, foundation primer, glimmers & shimmers, powders, eye shadow, eye color, eye liner, mascara, nail polish, nail treatments-strengtheners, make-up, body creams, moisturizers, suntan preparations, sunless tan formulations, body butter, body scrubs, make-up remover, shampoos, conditioners, dandruff control formulations, antifrizz formulations, straightening formulations, volumizing formulations, styling aids, hairsprays, hair gels, hair colors and tinting formulations, anti-aging creams, body gels, essential oils, creams, cleansers, soaps. In various embodiments of any one of the above cosmetics, $R_1$ is $(C_1\text{-}C_{20})$ alkyl. In other embodiments, $R_1$ is a $(C_1\text{-}C_6)$alkyl. In still other embodiments, $R_1$ is a $(C_7\text{-}C_{20})$alkyl. In various embodiments of any one of the above embodiments, $R_2$ is hydrogen. In other embodiments, $R_2$ is iodide. In still other embodiments, $R_2$ is hydroxyl.

A further embodiment introduces a mechanism to retard complex formation following preparation of the humic acid derivative's carboxylic groups to salts of sodium, calcium, etc. which would free other antioxidant active groups to be effective food preservative anti-oxidants. This is similar to using calcium or sodium salt of ascorbic acid as antioxidants instead of ascorbic acid.

Consumer interest in and awareness of the health properties of antioxidants has been increasing in recent years. This has simultaneously increased global sales of antioxidants (whether used as a food preservative or to provide a health enhancing or functional benefit) and foods that are recognized as being naturally rich in antioxidants. Notable examples include certain varieties of fruit such as blueberries and blackberries. As the sector has developed, antioxidants are now being used in the manufacture of a greater variety of foods to cater for increasingly health-conscious consumers. This has been most apparent in sectors such as chocolate confectionery, soft drinks, and hot beverages such as tea.

The humic acid derivatives are more efficient (based on humic acid studies) and cost effective compared to all other food antioxidants. Humic acid and its derivatives would be cheaper to manufacture than ascorbic acid and synthetic antioxidants and have greater thermal stability convenient for almost all food processing and cooking up to 350° C. and have the ability to dissolve and bond minerals and other nutritional elements with enhanced bioavailability.

EXAMPLES

Although the present technology has been described in considerable detail with reference to certain preferred embodiments thereof, other versions are possible. Therefore the spirit and scope of the appended claims should not be limited to the description and the preferred versions contained within this specification. Various aspects of the present technology will be illustrated with reference to the following non-limiting examples.

Example 1: Preparation of Antioxidant Compounds from Humic Acid

Preparation of the cleavage products of humic acid extracted from non-polluted marsh soils with an organic content of 30-35%. The alkaline extracted humic acid from marsh soils or forest soils was suspended in 25-40% HI solution in a stoichiometric equivalent ratio to the ether groups of humic acid weight ratio of 1:10. The humic acid underwent cleavage in the presence of sodium hypophosphite (10% of the HI), added to prevent further iodination of the aromatic phenolic structures and prevents oxidation of iodine ions.

The reaction was heated to reflux. The humic acid suspension began to cleave after 45 minutes and the solution became colored. The color changed progressively with reflux time. Fractions were taken 15 minute intervals until all the humic acid suspension disappeared (approximately after 10 hours depending on the concentration of HI) until a homogeneous reaction mixture was obtained.

Fraction products were neutralized or transferred to the carboxylate salts (Na, Ca, Mg, Mn, and similar salts.) by neutralizing the carboxylic acid groups with required alkaline hydroxides or carbonate.

The reaction matrix compositions mixture were characterized by TLC (Thin Layer Chromatography), pH titration, IR, NMR and molecular weight determination for some of the fractions.

The TLC displayed at least 12 spots using different solvent carriers, indicating the presence of at least 12 compounds in the final reaction mixture. This is in a good agreement with the chemical structure evaluation in addition of presence of low aromatic carboxylic acids and hydroquinone derivatives.

Example 2: Preparation of Humic Acid Antioxidant Compounds using Nickel Catalysis The bond cleave of Example 1 is carried out by nickel catalyzed hydrogenolysis. The humic acid is dissolved in 3-octenone or other solvents or mixed solvents in the presence of nickel carbine complex under one bar of hydrogen at a temperature of 80-120° C. (See, for example, Sergeev, et al., *Science,* 332(6028), p 439-43).

Example 3: Preparation of Humic Acid Antioxidant Compounds using Sodium Borohydride The bond cleave of Example 1 is carried out by action of sodium borohydride. Humic acid is dissolved in a solution of sodium hydroxide in 1:1 ethanol: water in the presence of Ni—Cr-boride where sodium borohydride is formed in situ. The reaction takes place at atmospheric pressure. (See, for example, Marton, et al., *Acta Chem. Scand.* 15(2), p. 370-83, 1961).

Example 4: Preparation of Humic Acid Antioxidant Compounds using Lithium Chloride The bond cleave of Example 1 is carried out by action of lithium chloride in dimethyl formamide Humic acid is dissolved in a solution of LiCl-DMF at boiling conditions for 4-72 hours. (See, for example, Fang, et al., J. Mol. Catalysis A: Chemical, 274(1-2), p. 16-23, 2007; Bernard, et al., *Synthesis,* 1989(4), p. 287-89).

Example 5: Preparation of Humic Acid Antioxidant Compounds using Hydrogen Iodide The bond cleave of Example 1 was carried out by action of hydrogen iodide. The humic acid was reacted with aqueous hydrogen iodide and sodium hypophosphite to form a suspension. Alternatively, the suspension was heated until a substantially homogeneous reaction mixture was obtained. In yet another alternative, the heating was carried out at reflux temperature.

Example 6: Preparation of Humic Acid Antioxidant Compounds using Hydrogen Bromide The bond cleave of Example 1 was carried out by action of hydrogen bromide. Humic acid was dissolved in an organic solvent such as methyl ethyl ketone or a mixture of solvents, then this mixture was added to an aqueous solution consisting of glacial acetic acid and concentrated hydrogen bromide at 0-10° C. in the presence of 1% surfactant (Cetrimide). The cleavage was carried out in an emulsion system under efficient mixing for 5 hours. At the end of five hours, the temperature was raised to 25° C. The reaction was continued for an additional hour.

Example 7: Thermal Degradation Stability Comparison of Stabilized PVCs and PVC The cleaved product mixture, its salts, and chelates are evaluated as antioxidants and thermal stabilizers for PVC, low density polyethylene, and polyvinyl alcohol as a model to evaluate the anti-oxidation efficiency using thermal analysis (differential scanning calorimetry (DSC) and thermo gravimetric analysis (TGA)) techniques, including differential thermogravimetry (DTG) to determine the decomposition temperature. The chelates with several transition metal ions show remarkable efficiency for thermo-oxidative stabilization of PVC. Typical results are provided in Table (1). Tests using 1% of the calcium salt of the hydrolyzed humate mixture in extruded PVC showed higher stabilizing efficiency than 1% of humic acid in extruded PVC. Both are better than PVC extruded without an antioxidant. The PVC stabilized with 1% of the calcium salt of the humate hydrolyzed mixture develops a golden and orange color as compared to PVC stabilized with humic acid which is very dark color not suitable as food packaging additive.

TABLE (1)

Thermal degradation stability of PVC and stabilized PVCs

| | HCl % (loss) from TGA | | |
|---|---|---|---|
| Temperature, ° C. | PVC control (K value 70) | PVC with 1% Humic acid | PVC with +1% Ca-Humate hydrolyzed mixture |
| 250 | 3 | 1 | 0 |
| 260 | 5 | 2 | 0 |
| 270 | 10 | 2 | 0.5 |
| 280 | 33 | 5 | 1.0 |
| 290 | 1 | 13 | 1.0 |
| 300 | 47 | 35 | 5.0 |
| Total HCl loss (%) at Decomp. Temp. | 63 | 57 | 53 |
| Decomp. Temp., ° C., from DTG | 265 | 280 | 310 |
| Rate of decomposition at Decomp. Temp. %/min | 1.63 | 1.09 | 0.73 |

Example 8: Humic Acid Derived antioxidants as Stabilizers of Canola Oil

Unfortified canola oil (100 g) is thoroughly mixed with 400 mL of deionized water and 10 g of polysorbate-20 (Tween 20). The blended emulsion is homogenized and then stored at 60° C. Emulsion solutions containing various concentrations of antioxidant extracts are prepared and incubated at 60° C. on an orbital shaker along with control treatments without antioxidants. Measurements are taken once a day, for several consecutive days by measuring the UV absorbance of the conjugated dienes of the canola oil at 234 nm. The absorbance (at A=234 nm) plotted against time shows the canola oil treated with the antioxidants derived from humic acid are effective.

Example 9: Humic Acid Derived Antioxidants as Stabilizers of Margarine

Margarine samples are prepared, containing: the instant humic acid antioxidant compounds (200 ppm), and no antioxidants (control), and incubated at 22-23° C., in the dark. Margarine samples of each treatment are pulled periodically, and the fat is separated by melting at 60° C., followed by centrifuging at about 1,000 g and decanting the upper (fat) phase. Oxidation is evaluated by measuring the peroxide value according to the AOCS official method Cd 8b-90. Results show that the instant antioxidant compounds inhibit oxidation in comparison to the untreated control, reflecting in lower levels of peroxide value (PV) over time.

Example 10: Humic Acid Derived Antioxidants as Stabilizers of Milk

Fresh milk is treated with the instant humic acid antioxidant compounds at 100 ppm, homogenized, spray-dried, then is incubated at room temperature (22-23° C.), in the dark, in comparison to the same spray-dried milk without any additives (control). Samples are analyzed periodically by gas chromatography, and oxidation is traced by monitoring the generation and accumulation of secondary oxidation products (e.g. hexanal). The experiment shows an antioxidative protective effect of the instant antioxidant compounds, reflected in lower levels of secondary oxidation products.

Example 11: Humic Acid Derived Antioxidants as Stabilizers of Cereal

Breakfast cereal consisting of 5% milled flax seed and 95% corn semolina, and 250 ppm of the instant antioxidant compounds, is compared to the same recipe without any antioxidant additives (control). Samples are incubated in the dark at room temperature (22-23° C.) for several weeks. The cereal sample containing the instant antioxidant compounds is more oxidatively stable as it exhibits lower levels of the oxidation markers as detected by gas chromatography.

Example 12: Stabilized Cosmetic Containing Epi-Gallo Catechin Gallate (EGCG) with Humic Cleavage Derivatives A stabilized cosmetic containing EGCG is made using humic acid derived compound II. Stearic acid (2.7 wt %), palmitic acid (2.7 wt %), 1-hexadecanol (5.4 wt %), 1-octadecanol (2.7 wt %), sorbitan monostearate (3.1 wt %), propylene glycol (18 wt %), glycerol (9 wt %), triton X-100 (18 wt %), carbomer (0.5 wt %) and compound V (0.4 wt %) are heated at 70 degree C. with constant stirring for an hour. EGCG (0.2 g) and 0.2 g of Humic cleaved derivatives are added and it is then heated and stirred for 15 min at this temperature. Distilled water (38 wt %), is then poured into the organic phase and homogenized for 15 minutes at this temperature. The composition prepared is laid in a chamber at room temperature for one week.

The composition is then analyzed by HPLC for identifying the retained amount of the EGCG. The HPLC (high pressure liquid chromatography) with UV (274 nm) detectors is used for the analysis for EGCG content in the formulation. The EGCG is extracted from the compositions by the extraction of 100 mg of said formulation with 2 mL of distilled water with constant shaking. An aliquot is filtered directly into an HPLC-vial using a membrane filter and 20 microliters injected into the HPLC system. Integration, calibration and calculation are automatically performed with the software and the retention time of EGCG and its calibration is completed by the co-injection of standard 1%

EGCG aqueous solution for each HPLC analysis. The resulted data of HPLC shows that most EGCG is left without change one week later.

Example 13: Stabilization of Polyethylene for Food Packaging

Polyethylene films are prepared with 0.1% by weight and with 0.5% by weight of humic acid, derivatives, cleaved salts, and chelates by extrusion methods to form films for food packaging. The films are subjected to natural sun light in Sydney, Australia, and with high UV light for 4 weeks. The resultant films are tested by IR and UV spectrometry. The films stabilized with metal chelates show no color change and no spectral changes while unstabilized polyethylene samples as controls show change in coloration and absorption spectra.

Example 14: Stabilization of Polyvinyl Chloride (PVC) for Food Packaging

PVC (K value 70) stabilized with 1% humic acid, derivatives, cleaved salts, and chelates (typical thermal stability characteristics listed in Table 1) are prepared by extrusion to form films for food packaging. The films are subjected to natural sunlight in Sydney, Australia, and with high UV light for 4 weeks. The stabilized films with metal chelates show no color change while control films of unstabilized PVC samples show change in coloration to a dark yellowish color.

What is claimed is:

1. An antioxidant compound selected from the group of at least one compound of a humic acid cleavage derivative, a salt, a chelate, or a combination thereof, wherein the humic acid cleavage derivative is selected from the group consisting of formula II, formula III, formula IV, formula V and formula VI:

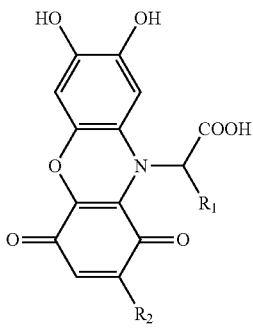

II

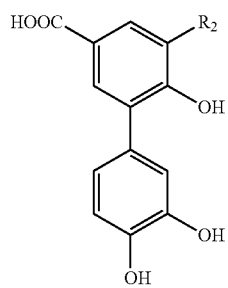

III

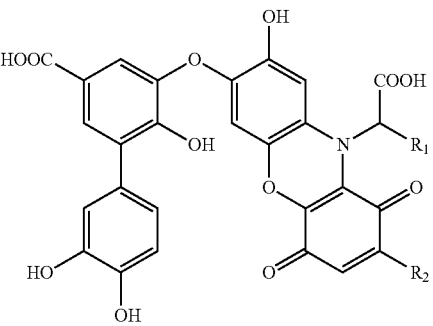

IV

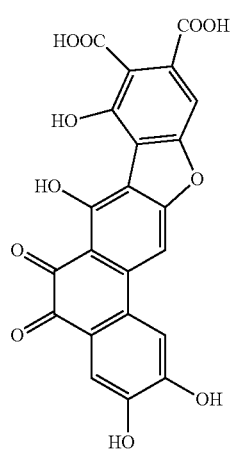

V

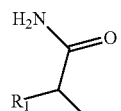

VI wherein:
  $R_1$ is alkyl or substituted alkyl; and
  $R_2$ is hydrogen, iodide, or hydroxyl.

2. The antioxidant compound of claim 1, wherein the compound is formula II, a salt, or a chelate thereof.

3. The antioxidant compound of claim 1, wherein the compound is formula III, a salt, or a chelate thereof.

4. The antioxidant compound of claim 1, wherein the compound is formula IV, a salt, or a chelate thereof.

5. The antioxidant compound of claim 1, wherein the compound is formula V, a salt, or a chelate thereof.

6. The antioxidant compound of claim 1, wherein the compound is formula VI, a salt, or a chelate thereof.

7. The antioxidant compound of claim 1, wherein $R_1$ of the humic acid cleavage derivative of formula II, formula IV, and formula VI is a $(C_1-C_{20})$ alkyl.

8. The antioxidant compound of claim 1, wherein $R_2$ of the humic acid cleavage derivative of formula II, formula III, formula IV, and formula VI is hydrogen.

9. The antioxidant compound of claim 1, wherein $R_2$ of the humic acid cleavage derivative of formula II, formula III, formula IV, and formula VI is iodide.

10. The antioxidant compound of claim 1, wherein $R_2$ of the humic acid cleavage derivative of formula II, formula III, formula IV, and formula VI is hydroxyl.

11. The antioxidant compound of claim 1, wherein the compound is a lithium salt, sodium salt, ammonium salt, potassium salt, calcium salt, barium salt, magnesium salt, manganese salt, zinc salt, aluminum salt, iron salt, or a combination thereof.

12. The antioxidant compound of claim 1, wherein the compound is a transition metal ion chelate.

13. A method of preparing an antioxidant compound selected from the group of at least one compound of a humic acid cleavage derivative, a salt, a chelate, or a combination thereof, the method comprising:
  reacting a humic acid with a cleaving agent to form a reaction mixture,
  optionally heating the reaction mixture to about reflux to obtain a substantially homogeneous reaction mixture; and
  isolating at least one antioxidant compound of the humic acid cleavage derivative, a salt, or a chelate thereof, wherein the humic acid cleavage derivative is selected from the group consisting of formula II, formula III, formula IV, formula V, and formula VI:

II

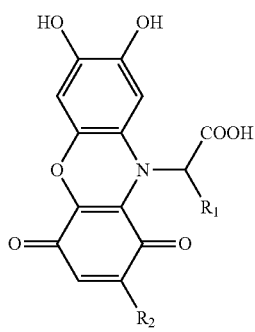

III

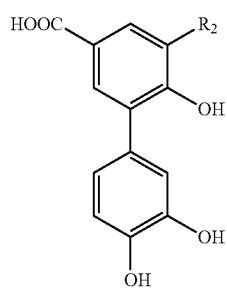

IV

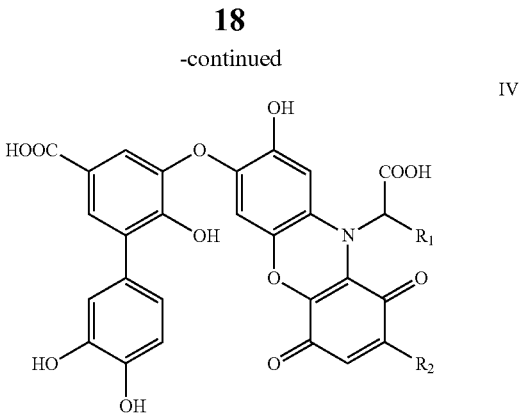

V

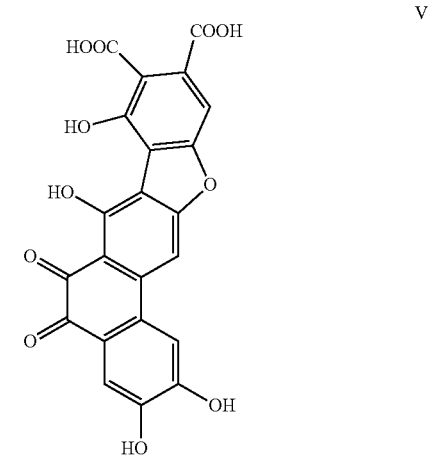

VI

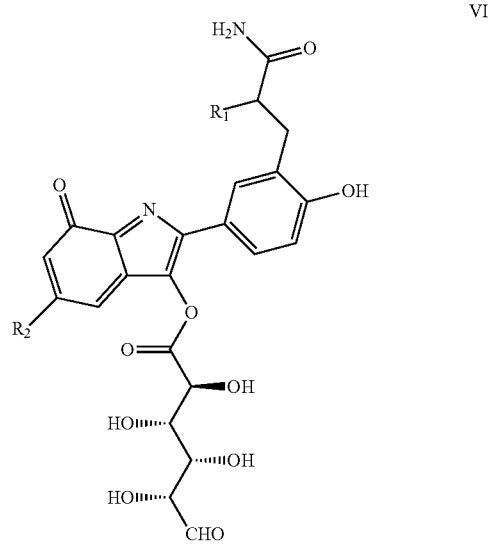

wherein $R_1$ is alkyl; and $R_2$ is hydrogen, iodide, or hydroxyl.

14. The method of claim 13, wherein the humic acid comprises at least one compound having substructure of formula I:

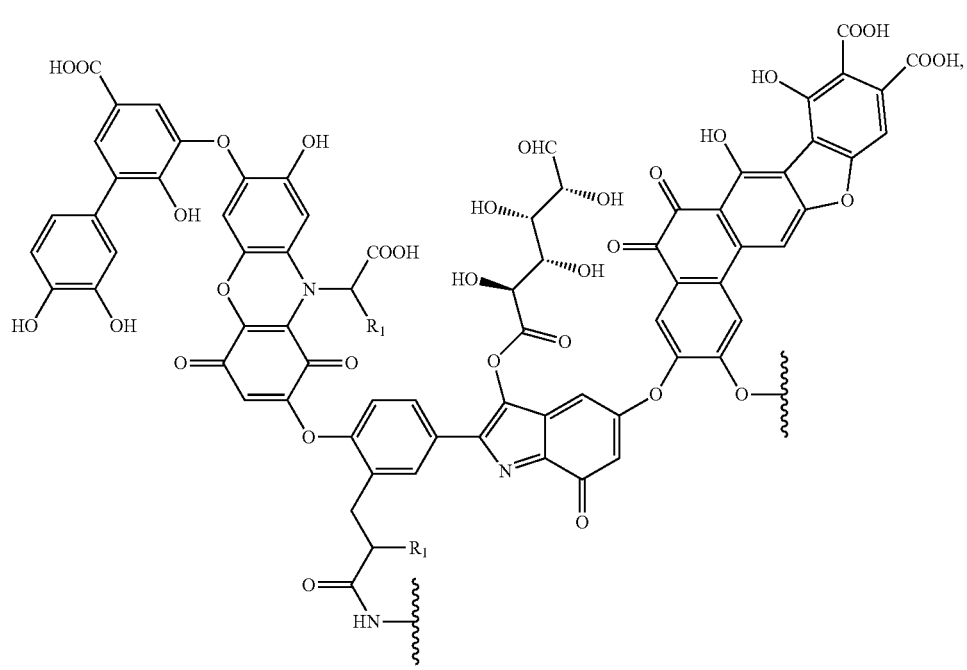

a salt, or a chelate thereof, wherein each $R_1$ is independently alkyl.

15. The method of claim 13, wherein the cleaving agent is selected from the group consisting of nickel catalyst, sodium borohydride, amide hydro halide salts, lithium chloride in dimethylformamide, hydrogen bromide, and hydrogen iodide.

16. The method of claim 13, wherein reacting the humic acid with the cleaving agent comprises reacting the humic acid with aqueous hydrogen iodide and sodium hypophosphite to form a suspension.

17. The method of claim 16, further comprising heating the suspension at about reflux until a substantially homogeneous reaction mixture is obtained.

18. The method of claim 13, further comprising isolating the salt of the at least one antioxidant compound of the humic acid cleavage derivative.

19. The method of claim 13, wherein isolating the at least one antioxidant compound of the humic acid cleavage derivative comprises isolating a salt of the antioxidant compound, and the salt is selected from the group consisting of a lithium salt, a sodium salt, an ammonium salt, a potassium salt, a calcium salt, a barium salt, a magnesium salt, a manganese salt, a zinc salt, an aluminum salt, and an iron salt.

20. The method of claim 13, wherein isolating the at least one antioxidant compound of the humic acid cleavage derivative comprises isolating a derivative where $R_1$ is a $(C_1-C_{20})$ alkyl.

21. The method of claim 13, wherein isolating the at least one antioxidant compound of the humic acid cleavage derivative comprises isolating a derivative where $R_2$ is hydrogen.

22. The method of claim 13, wherein isolating the at least one antioxidant compound of the humic acid cleavage derivative comprises isolating a derivative where $R_2$ is iodide.

23. The method of claim 13, wherein isolating at least one antioxidant compound of the humic acid cleavage derivative comprises isolating a derivative where $R_2$ is hydroxyl.

* * * * *

UNITED STATES PATENT AND TRADEMARK OFFICE
CERTIFICATE OF CORRECTION

| | | |
|---|---|---|
| PATENT NO. | : 9,932,319 B2 | Page 1 of 1 |
| APPLICATION NO. | : 14/894616 | |
| DATED | : April 3, 2018 | |
| INVENTOR(S) | : Adam et al. | |

It is certified that error appears in the above-identified patent and that said Letters Patent is hereby corrected as shown below:

In the Specification

In Column 3, Line 16, delete "term 'transition" and insert -- term "transition --, therefor.

In Column 4, Line 3, delete "C1-05" and insert -- C1-C5 --, therefor.

In Column 6, Line 51, delete "$R_1$ are" and insert -- $R_1$ is --, therefor.

In Column 12, Line 44, delete "formamide Humic" and insert -- formamide. Humic --, therefor.

In the Claims

In Column 15, Line 39, in Claim 1, delete "formula V and" and insert -- formula V, and --, therefor.

In Column 17, Line 31, in Claim 13, delete "mixture," and insert -- mixture, and --, therefor.

In Column 19, Line 49, in Claim 19, delete "and the" and insert -- and wherein the --, therefor.

Signed and Sealed this
Twenty-second Day of May, 2018

Andrei Iancu
*Director of the United States Patent and Trademark Office*